US011759327B2

(12) United States Patent
Bailey

(10) Patent No.: US 11,759,327 B2
(45) Date of Patent: Sep. 19, 2023

(54) DOME TOE RESURFACING SYSTEM

(71) Applicant: Erroll J Bailey, Atlanta, GA (US)

(72) Inventor: Erroll J Bailey, Atlanta, GA (US)

( * ) Notice: Subject to any disclaimer, the term of this patent is extended or adjusted under 35 U.S.C. 154(b) by 14 days.

(21) Appl. No.: 17/693,283

(22) Filed: Mar. 11, 2022

(65) Prior Publication Data
US 2022/0192839 A1    Jun. 23, 2022

Related U.S. Application Data

(62) Division of application No. 17/074,357, filed on Oct. 19, 2020, now Pat. No. 11,382,759.

(60) Provisional application No. 62/923,499, filed on Oct. 19, 2019.

(51) Int. Cl.
*A61F 2/42* (2006.01)
*A61B 17/16* (2006.01)
*A61F 2/30* (2006.01)

(52) U.S. Cl.
CPC ........ *A61F 2/4225* (2013.01); *A61B 17/1682* (2013.01); *A61B 17/1697* (2013.01); *A61F 2002/30112* (2013.01); *A61F 2002/30217* (2013.01); *A61F 2002/4233* (2013.01); *A61F 2310/00023* (2013.01)

(58) Field of Classification Search
CPC ....................... A61F 2/4225; A61F 2002/4233
See application file for complete search history.

(56) References Cited

U.S. PATENT DOCUMENTS

2013/0231744 A1*  9/2013  Taylor .............. A61F 2/28
                                                    623/16.11

FOREIGN PATENT DOCUMENTS

FR           3022137 A1  * 12/2015  ............. A61B 17/15

* cited by examiner

*Primary Examiner* — Javier G Blanco
(74) *Attorney, Agent, or Firm* — Lewis Brisbois Bisgaard & Smith LLP

(57) ABSTRACT

An innovative dome toe resurfacing system for performing metatarsophalangeal joint replacement is disclosed. The present invention comprises a prosthetic implant for metatarsophalangeal joint, and one or more cone extensions that covers portions of the prosthesis that extends into the metatarsal bone and phalanx bone. The cone extensions include a plurality of ridges that will catch bone on insertion and provide a press fit. The present invention also includes a cone and cup reaming system wherein one or more reamers will ream a cone/cup shape for the articular surfaces, and prepare the metatarsal and phalangeal canals for the insertion of the cone extensions. The cone extensions have ends that fit the reamed cone/cup shape wherein the cone/cup shape resembles the natural anatomy of articular surfaces of metatarsophalangeal joint.

1 Claim, 10 Drawing Sheets

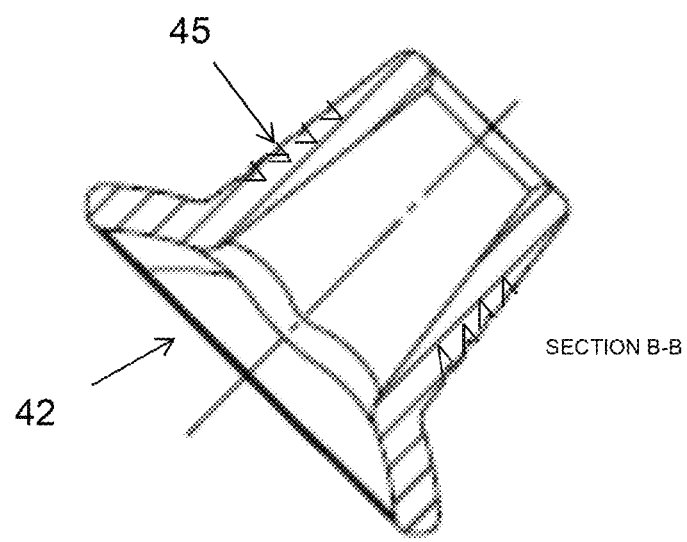
FIG 12
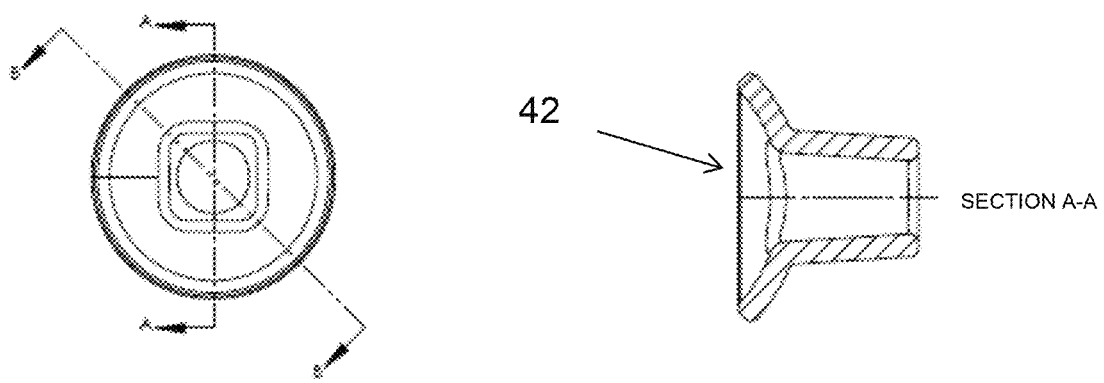
FIG 11
FIG 13

DOME TOE RESURFACING SYSTEM

CROSS-REFERENCE TO RELATED APPLICATION

This application claims the benefit of and priority from U.S. application Ser. No. 17/074,357 filed on Oct. 19, 2020 which claims the benefit of and priority from U.S. provisional application No. 62/923,499 filed on Oct. 19, 2019 and entitled Dome Toe Resurfacing System. The contents of the above application are hereby incorporated herein by reference in full.

FIELD OF INVENTION

This specification relates to a dome resurfacing system for metatarsophalangeal joint replacement.

BACKGROUND

The presently described invention provides an innovative dome toe resurfacing system for performing metatarsophalangeal ("MTP") joint replacement. The present invention provides an innovative system and method that will provide longer implant survival, reduce the incidence of wear, diminish the occurrence of silicone synovitis, reduce bone resection and bone loss, minimize metatarsalgia and yield better patient satisfaction. The present invention includes a prosthesis, i.e., a prosthetic implant, for metatarsophalangeal joint, and one or more cone extensions that covers portions of the prosthesis that extends into the metatarsal bone and phalanx bone. The cone extensions include a plurality of ridges that will catch bone on insertion and provide a press fit. The present invention also includes a cone and cup reaming system wherein one or more reamers will ream a cone/cup shape for the articular surfaces, and will also prepare the metatarsal and phalangeal canals for the insertion of the cone extensions. The cone extensions have ends that fit the reamed cone/cup shape wherein the cone/cup shape resembles the natural anatomy of articular surfaces of metatarsophalangeal joint.

Hallux rigidus is a progressively painful, degenerative condition of the hallux MTP joint. It is characterized by loss of motion, periarticular osteophyte formation, cartilage wear and ultimately eburnation of the joint surface. Initial conservative management includes activity and shoe wear modifications, carbon fiber inserts, anti-inflammatory drugs and steroid injections. For early stages of the disease, there have been a variety of joint-sparing procedures that have been described. These include cheilectomy, distal metatarsal or proximal phalanx dorsiflexion osteotomies and interposition arthroplasty. For advanced disease, first MTP joint arthrodesis has been a reliable treatment option with high patient satisfaction. This procedure, however is not without its complications, with rates of up to 10% for nonunion, 14% for reoperation and 10% for metatarsalgia.

Historically, total joint implant arthroplasty has demonstrated somewhat poor results. Recent hemiarthroplasty with metallic or polyvinyl alcohol hydrogel implants have demonstrated encouraging results. Moreover, despite popular orthopedic belief, second generation and third generation silastic implants have an excellent seven-year survival rates of 97%.

Medical grade silicone was first introduced by Dow Corning in 1955 under the brand name of Silastic. There were a number of applications in humans for this material. A shunt for hydrocephalus was the first. Then, in the hand, in 1967, Swanson used silicone as a single stemmed implant. This implant was later modified for the foot and became the first MTP joint implant (hemi implant) used in conjunction with a Keller procedure.

Early hemi implants were primarily rigid material used for the replacement or resurfacing of the first metatarsal head. These implants frequently loosened or dislocated due to osteoporosis and bone resorption. It was then hypothesized that softer, more flexible materials would possibly give rise to better outcomes. When Swanson designed his hemi implant for the phalanx side of the joint and chose silicone, it gained wide acceptance in the 1970's and early 1980's, but then came the problems. Complications included granulomatous reactions, lymphadenitis, synovitis, bone cyst with fibrous hyperplasia, osteolysis, ectopic bone growth, implant failure and biomechanical joint failure. Something had to be done, so Dow Corning changed its physical properties to increase tear resistance, tensile strength and tear propagation. It was called Silastic HP. This new development showed decreased abrasion resistance but was deemed inappropriate for a hemi implant. However, because of its increased strength, it was well suited for Swanson's double stemmed, flexible hinge design. These implants performed remarkably better but did show increased wear at the implant bone interface and thus metal titanium grommets were added to reduce this wear. It took years and consistent failure of hemi implants to abandon them and move consistently into double stemmed hinged implants.

If hemi implants are classified as the first generation of MTP joint implants, then these newer double-stemmed flexible hinged implants were classified as second generation. Older, less active patients with low functional demands have shown reasonably consistent, successful outcomes with second generation prostheses.

A recent article in 2019 by Timothy Clough and Joseph Ring in the British Bone and Joint Journal looked at 108 consecutive Swanson double stemmed implants (Wright Medical, Memphis Tenn.) in 76 patients between January 2005 and December 2016 with a minimum follow up of two years. The average age was 61.4. The survivorship at a mean follow-up of 5.3 years was 97.2%. The patient satisfaction rate was 90.6%. Three implants required revisions (2.8%), one got infected and two stems broke at 10.4 and 13 years respectively. There was a 1.9% reoperation rate other than revision, 23% of patients had very minor complications and 21.1% had non-progressive, asymptomatic cysts on radiological review. This is the most successful result in the literature for second generation implants that exists. It should be noted however, that overwhelmingly with "other" peer review articles about 2nd generation implants, even though patient satisfaction rates were high (80-90%), metatarsalgia, silicone synovitis and bone loss complications were fairly significant and concerning. They were far from perfect. Thus, the need for improvement.

With the aid of computer modeling and finite element analysis, the first third generation implant, the Primus, was developed by Futura Biomedical in 1998. These computer models showed a need for an axial offset hinge. All 2nd generation implants were similar to hand implants with both of the bone-engaging surfaces coming off the hinge as though the first metatarsal and phalanx sat equally on the weight bearing surface. No one had thought about the fact that because of the sesamoids, the metatarsal head sits more dorsal to the phalanx base. This situation stressed the hinge and created a hallux elevates situation, both of which would lead to increased wear. The Primus offset axial hinge dealt with both of these issues. Moreover, a better silicone elastomer called UltraSil, with improved properties over Silastic HP, was created during this time which contributed to the forward push and resurgence of these implants. The combination of computer modeling, improved silicone material with grommet shielding and more precise instrumentation all contributed to the durability of the implant and improved joint function.

Lawrence and Thuen in 2013 reviewed 201 Primus implants in 144 patients with an average follow up of 66.4 months. Seventy implants in 54 patients were available for clinical evaluation. Only 2 implants were removed and these were for issues other than implant breakdown. Patient satisfaction scores (AOFAS score) were high at 88.

A similar study by Fieschi and Saffarini from Switzerland in 2016 reported midterm outcomes of a 3rd generation implant (Primus) at 5 yrs. Seventy implants in 64 patients were evaluated. The indications were grade 2 hallux rigidus (10%) and grade 3 (87%) or revision surgery (2.9%). The AOFAS median score was 90. In terms of the most common complication, metatarsalgia, the patients exhibited "mild" in 41.1%, moderate in 7.1% and severe in 1.4%. Metatarsalgia was absent in 47.1%. This study again confirmed the findings of excellent midterm clinical outcomes and survival rates with third generation prostheses.

Majeed, in EFFORT Open Reviews (the British Editorial Society of Bone and Joint Surgery) 2019, published a comprehensive paper that reviewed all articles in the literature that dealt with outcomes of silastic implants. 522 studies were found. Using the criteria of at least 7 years follow up with a certain number of patients per study, 28 articles were selected for inclusion. There was one prospective study and all others were retrospective studies. Twenty-eight papers had a total of 2354 feet with silastic replacements in 1884 patients. The studies took place and their outcome results were collected between 1968 and 2003. The average age of patients was 53 with the youngest being 15 and the oldest 82 years old in different studies. The average follow-up was 85.3 months. These included single stemmed and double stemmed prosthesis. Among all the studies, there were a total of 5.3% (124) failed prosthesis. Of note is the fact that single stemmed failed at 11% while double stemmed failed at 3.6%. Hence, the reason why only double stemmed silastic HP implants are the only ones in use. There was a reported incidence of 3.6% (85 feet) of superficial infection, early inflammation of the wound and synovitis. Deep infection rate was 1.7% (40 feet). Radiological lucencies, cyst formation, bone resorption and osteophyte formation, of varying degree, was in 18.2% of cases (429 feet), although these findings did not correlate with patient outcomes. Implant fracture and fragmentation occurred in 4.3% (101 feet). Eighty-four implants (3.6%) required removal due to infection, fracture or persistent pain after surgery. Three studies assessed the use of titanium grommets with double stemmed implants. Two of these studies reported a higher incidence of radiological lucencies and implant failure without the use of grommets and recommended that grommets be used routinely, while the third study did not find any significant differences with the outcomes of implants with or without the use of grommets. Currently in orthopedic and podiatric practices today, overwhelmingly, grommets are used.

The present invention, Dome Toe Resurfacing System ("DRS"), is a unique design that would improve what is already a somewhat proven entity. The DRS uses the prosthesis that differs from the previous in the following ways. First, instead of the usual short grommet, the DRS will incorporate a "cone" extension over the silastic implant covering it in its entirety in the metatarsal shaft and proximal phalanx. The terminal end of each may or may not completely encase the silastic. These cone extensions will have a set of ridges on each side that will catch bone on insertion and provide a press fit. Second, instead of flat cuts on the metatarsal and phalanx (the usual way things are done), the innovative DRS will use a cone and cup reaming system. The reamers will have a dual function: it will ream a cone/cup shape for the articular surfaces, it also will incorporate a central extension that will also prepare the metatarsal and phalangeal canals for the cone shaped extensions. Third, because of the cone and cup anatomy, the silastic implant will have ends shaped as such to essentially "resurface" the articular surfaces, resembling more of our normal anatomy. Fourth, instead of a single offset hinge as the center of rotation, the prosthesis will have potential options for a single or multiple hinge concept thus better mimicking normal metatarsophalangeal joint biomechanical motion.

The above changes will provide for longer implant survival, reduce the incidence of wear, diminish the occurrence of silicone synovitis, reduce bone resection and bone loss, minimize metatarsalgia and yield better patient satisfaction. In addition, in instances where the implant has to be removed and the patient fused, the bone stock remaining for fusion will make for an easier and more successful rate of fusion (revision of current on the market prosthesis presents with marked bone loss makes fusions difficult and results are poor).

Swanson first thought that bone erosion and silicone synovitis occurred because of friction at the prosthetic bone interface. He introduced titanium grommets at the openings of the bones to reduce that interaction. They also have been proven to reduce the incidence of osteophyte formation at the ends of the bones. When viewing radiographs years out from implantation, it is relatively common to see cysts in the bone as well as radiolucencies and wear around the stem of the exposed silastic implant outside of the grommets on both sides. When these are revised, there is significant bone loss and a granulomatous inflammatory tissue reaction that has to be removed which weakens the bone. The DRS cone extension will cover the length of the implant and thus shield the silastic from the bone and consequently reduce bone reactions. In addition, the press fit features of the DRS cone will add stability to the construct also contributing to less wear. Currently used titanium grommets often wobble on both the metatarsal and phalangeal sides with motion at the joint. They are short and do not press fit.

Metatarsalgia, pain under the metatarsal heads (particularly the second metatarsal) is a common post-operation complication. This is usually caused by two things. First, too much bone is resected. Biomechanically, shortening alone of the 1st metatarsal makes the second metatarsal relatively longer, which makes it bear more weight, leading to pain. Second, if too much bone is resected at the base of the proximal phalanx, the attachment of the flexor hallucis brevis is weakened, and this leads to a reduction of great toe plantarflexion. The toe floats up and this leads to the second metatarsal overload and pain. The DRS system has cone and cup reamers that mimic normal anatomy with minimal bone resection and thus preserving length of the bone and also the attachment of the flexor brevis tendon. Both of these effects reduce the incidence of the second metatarsalgia.

SUMMARY

It is an objective of this invention to provide an innovative method and system for performing metatarsophalangeal joint replacement.

It is a further objective of this invention to provide a system and method that will provide longer implant survival, reduce the incidence of wear, diminish the occurrence of silicone synovitis, reduce bone resection and bone loss, minimize metatarsalgia and yield better patient satisfaction.

It is a further objective of this invention to provide a prosthesis that will better mimic the normal metatarsophalangeal joint biomechanical motion.

It is a further objective of this invention to provide a system and method that will reduce bone reactions with prosthetic implants.

These and other objectives are preferably accomplished by providing a dome toe resurfacing system ("DRS") comprising a prosthesis, i.e., a prosthetic implant, for metatarsophalangeal ("MTP") joint, and one or more cone extensions that covers portions of the prosthesis that extends into the metatarsal bone and phalanx bone. The cone extensions include a plurality of ridges that will catch bone on insertion and provide a press fit. The DRS includes a cone and cup reaming system wherein one or more reamers will ream a cone/cup shape for the articular surfaces, and will also prepare the metatarsal and phalangeal canals for the insertion of the cone extensions. The cone extensions have ends that fit the reamed cone/cup shape wherein the cone/cup shape resembles the natural anatomy of articular surfaces of MTP.

The procedure for using the DRS is as follows. A dorsal incision over the first MTP joint will be done. Soft tissue dissection down to the joint will be done and the joint will be exposed. The proximal phalanx will be plantarflexed to allow insertion of a 0.062 K Wire down the first metatarsal shaft. The dual function metatarsal cannulated reamers will be used to drill over the wire, preparing both a dome surface as well as a cone shaped canal in preparation to receive the silastic prosthesis. With the proximal phalanx in the same position, a 0.062 K Wire is then placed down the canal of the phalanx, and dual function reamers are used here as well. A trial prosthesis may be placed into the joint and range of motion and fit are assessed. The surgeon should err on under reaming (taking less bone) and if the fit is too tight, more bone can be taken, usually from the metatarsal side. Once the fit of the trial prosthesis is satisfied, then the cone extensions will be placed in the metatarsal and phalanx. The silastic implant is then introduced. Copious irrigation follows with closure of the wound.

The DRS will increase implant survivorship by providing a more stable and anatomic construct. The press fit, long titanium cone extensions will reduce intramedullary wear, bone cysts and osteophyte formation. It will reduce the incidence of the most common complication, metatarsalgia by preserving length. All of the above will lead to better clinical results and better long-term outcomes.

These and other aspects of this invention will become apparent to those skilled in the art after reviewing the following description of the invention.

BRIEF DESCRIPTION OF THE DRAWINGS

FIG. 11 is a top view of the cone extension described in FIG. 9 with cross-section lines A and B shown;

FIG. 12 is a cross-section view along line B of the cone extension described in FIG. 11;

FIG. 13 is a cross-section view along line A of the cone extension described in FIG. 11;

DETAILED DESCRIPTION AND PREFERRED EMBODIMENT

The detailed description of exemplary embodiments herein makes reference to the accompanying drawings and figures, which show the exemplary embodiments by way of illustration and best mode. While these exemplary embodiments are described in sufficient detail to enable those skilled in the art to practice the invention, it should be understood that other embodiments may be realized and that logical changes may be made without departing from the spirit and scope of the invention. Thus, the detailed description herein is presented for purposes of illustration only and not of limitation. Moreover, any reference to singular includes plural embodiments, and any reference to more than one component may include a singular embodiment.

Figure 1:
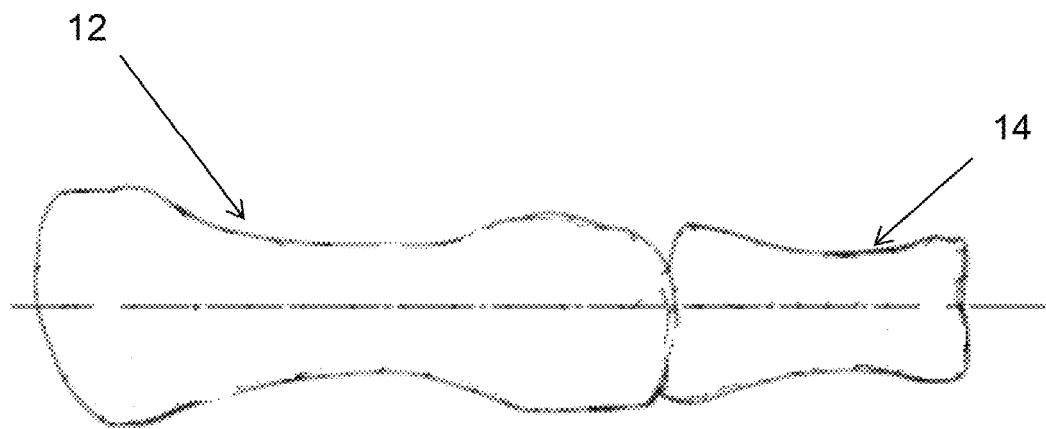
FIG. 1 is a top view of a first metatarsal bone and a phalanx bone anatomy.
Figure 2:
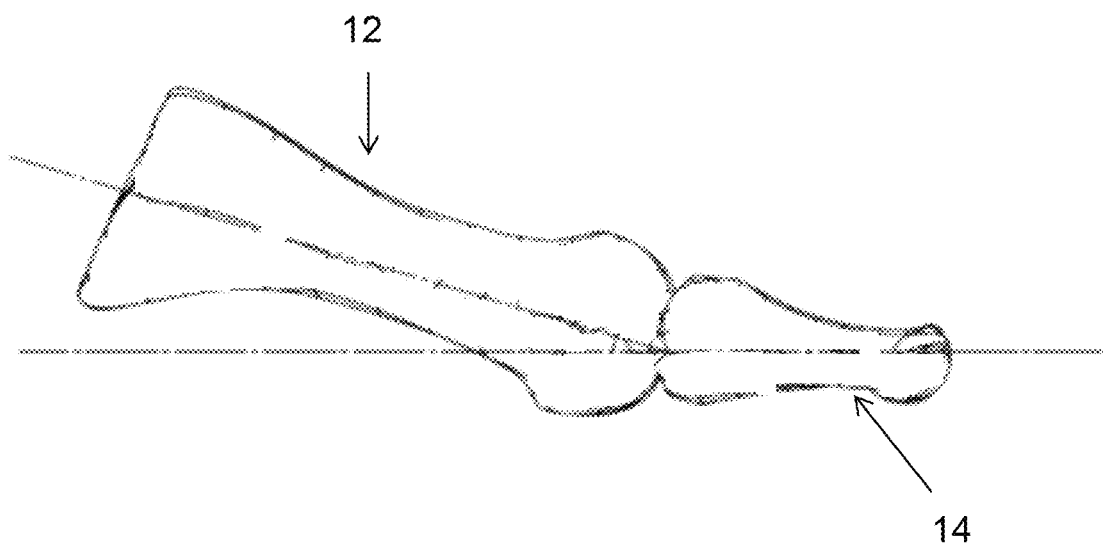
FIG. 2 is a side view of the first metatarsal bone and phalanx bone anatomy described in FIG. 1 when the foot rests on a flat surface.

FIGS. 1 and 2 describe top and side views of a first metatarsal bone 12 and a phalanx bone 14 anatomy of a human foot. As shown in FIG. 2, the first metatarsal bone 12 tilts slightly upward when the foot rests on a flat surface.

Figure 3:
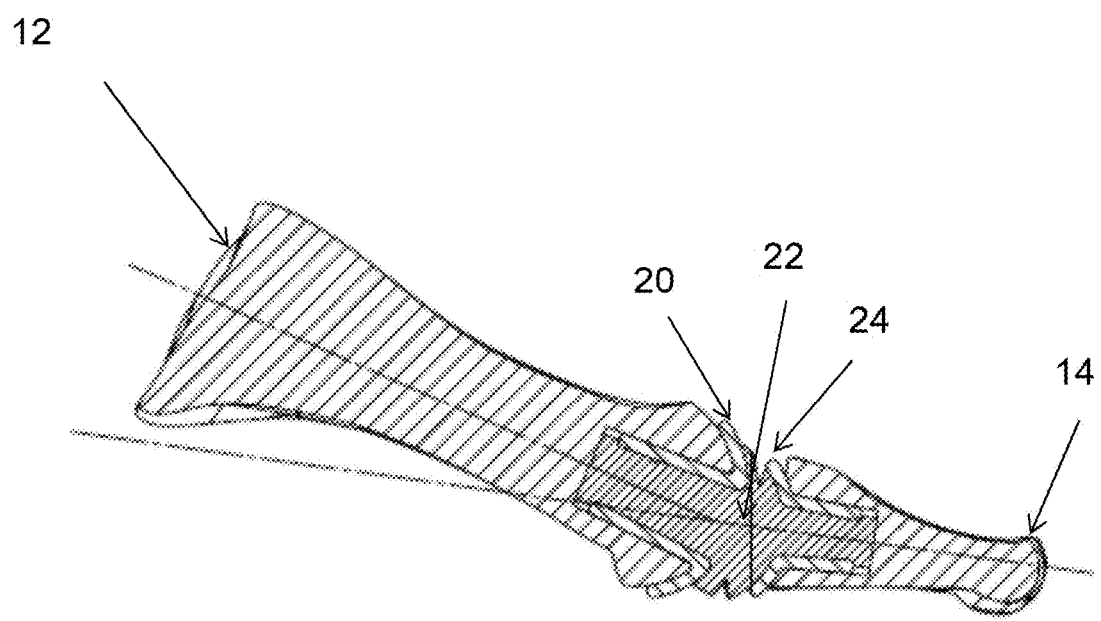
FIG. 3 is a side view of an embodiment of the present invention as implanted to a metatarsophalangeal joint.
Figure 4:
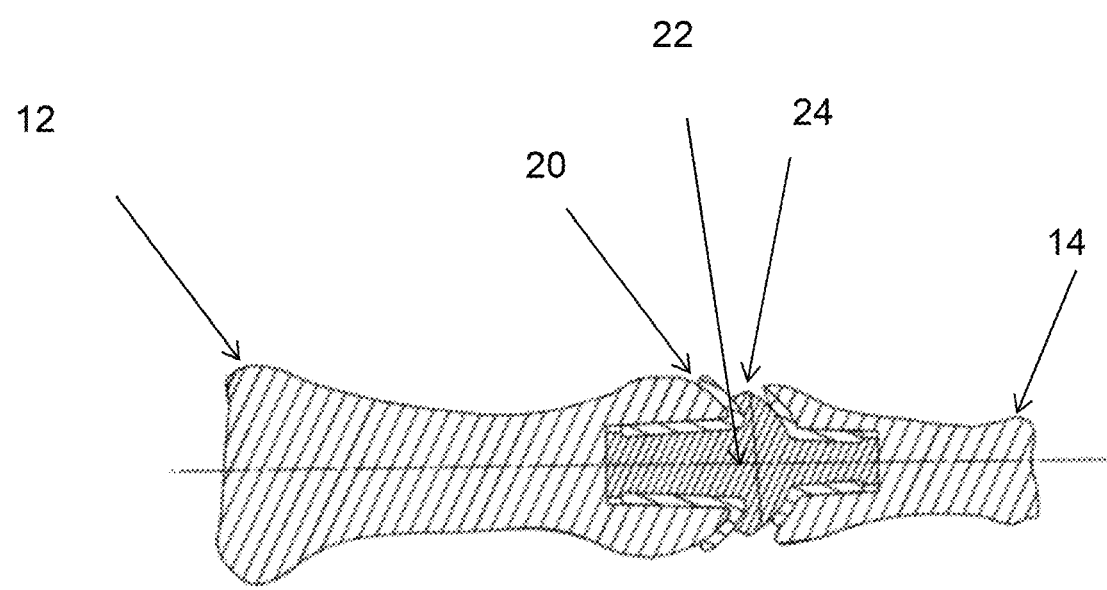
FIG. 4 is a top side view of an embodiment of the present invention as implanted to a metatarsophalangeal joint.

FIGS. 3 and 4 describe an embodiment of the present invention as implanted to a metatarsophalangeal joint. A cone extension 20 is implanted into a first metatarsal bone ("M-Cone"), and another cone extension 24 is implanted into a phalanx bone ("P-Cone"). The cone extensions 22, 24 are preferably made from rigid and durable material such as titanium. An elastomeric prosthesis 22, i.e., prosthetic implant, is inserted into a first metatarsal bone 12 and a phalanx bone 14 through the M-Cone 22 and P-Cone 24.

Figure 5:
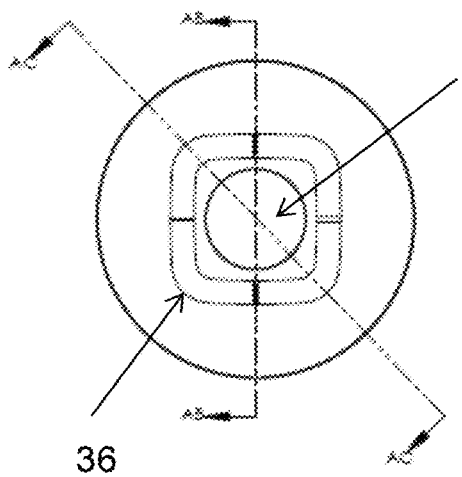
FIG. 5 is a top view of an embodiment of the cone extension of the present invention.
Figure 6:
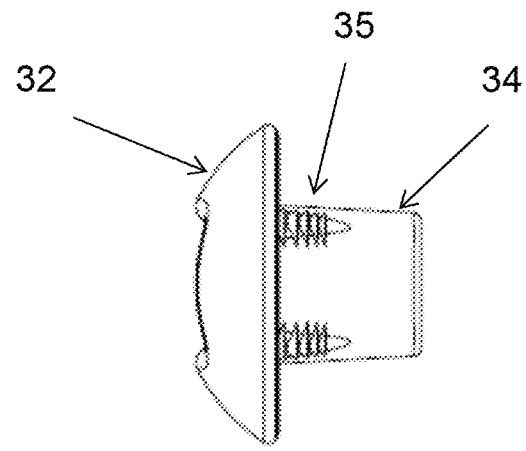
FIG. 6 is a side view of the cone extension embodiment described in FIG. 5.

FIGS. 5 through 8 disclose details of M-cone 22. As shown in FIGS. 5 and 6, the M-Cone comprises a generally dome shape top cover 32, a generally square column 34 with rounded corners 36 and a canal 38 at its center. One or more ridges 35 are located around each corner such that the ridges can grip the metatarsal bone and the M-Cone can press-fit into the metatarsal bone.

Figure 7:
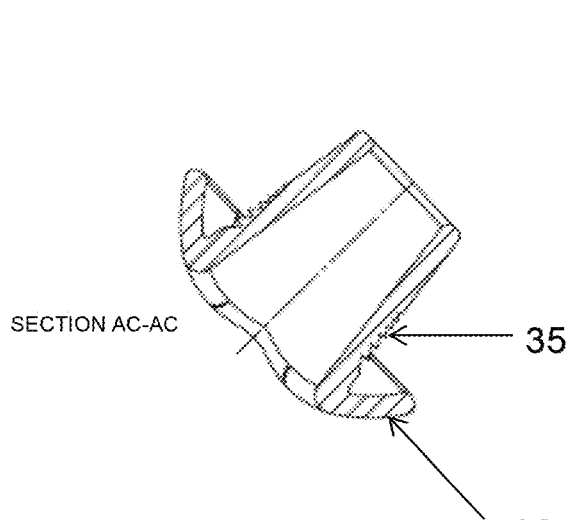
FIG. 7 is a cross-section view along line AC of the cone extension described in FIG. 5.
Figure 8:
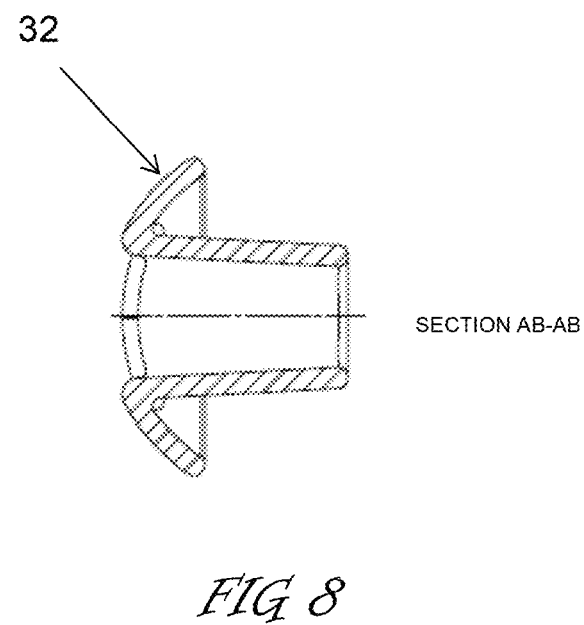
FIG. 8 is a cross-section view along line AB of the cone extension described in FIG. 57.

FIGS. 7 and 8 describe the interior of the M-Cone through cross-section views. As shown in FIGS. 7 and 8, the dome shape top cover 32 includes a concave under surface such that the M-Cone, when implanted, essentially caps the end of the metatarsal bone that joins the phalanx bone. The top surface of the dome shape top cover 32 is concave near its center along the diagonal cross-section line AC (FIG. 7) while the top surface is convex along the cross-section line AB (FIG. 8). The contour of the top surface of the dome shape top cover 32 mimics the natural anatomy of articular surface of the metatarsal bone in order to reduce bone resection.

Figure 9:
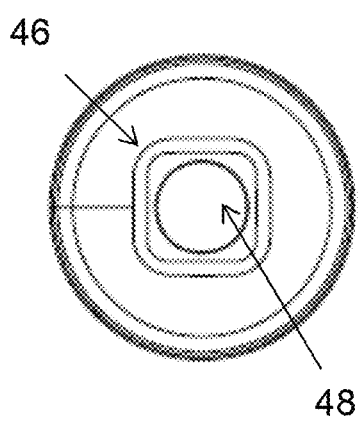
FIG. 9 is a top view of another embodiment of the cone extension of the present invention.
Figure 10:
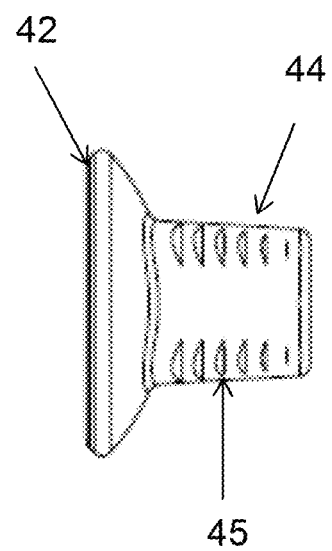
FIG. 10 is a side view of the cone extension embodiment described in FIG. 9.

FIGS. 9 through 13 disclose details of P-cone 24. As shown in FIGS. 9 and 10, the P-Cone comprises a generally concave top cover 42, a generally square column 44 with rounded corners 46 and a canal 48 at its center. One or more ridges 45 are located around each corner such that the ridges can grip the phalanx bone and the P-Cone can press-fit into the phalanx bone.

FIGS. 12 and 13 describe the interior of the P-Cone through cross-section views. See also, FIG. 11 for locations of cross-sections. As shown in FIGS. 12 and 13, the concave top cover 42 includes a convex under surface such that the P-Cone, when implanted, essentially fits the end articular surface of the phalanx bone that joins the metatarsal bone. The contour of the top surface of the concave top cover 42 mimics the natural anatomy of articular surface of the phalanx bone in order to reduce bone resection.

Figure 15:
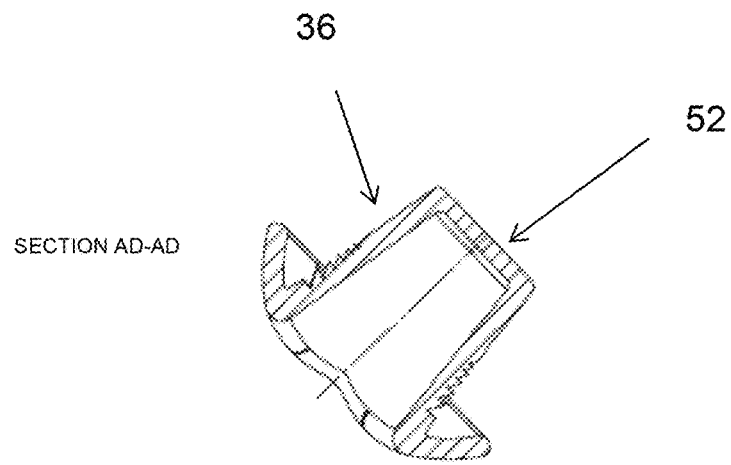
FIG. 15 is a cross section view along line AD of the cone extension described in FIG. 14.
Figure 14:
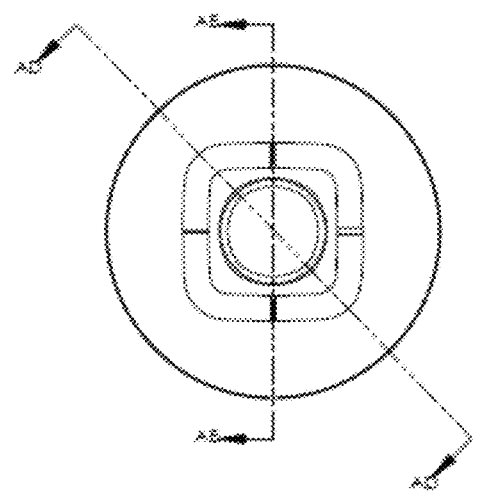
FIG. 14 is a top view of another embodiment of the cone extension of the present invention with cross section lines AB and AD shown.
Figure 16:
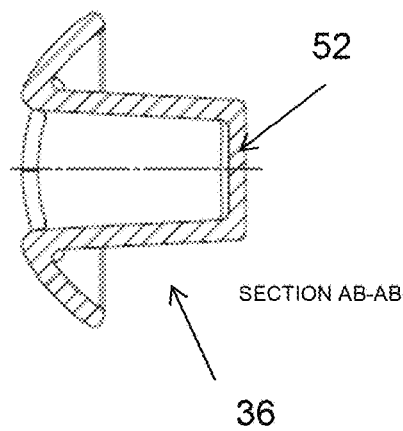
FIG. 16 is a cross section view along line AB of the cone extension described in FIG. 14.
Figure 18:
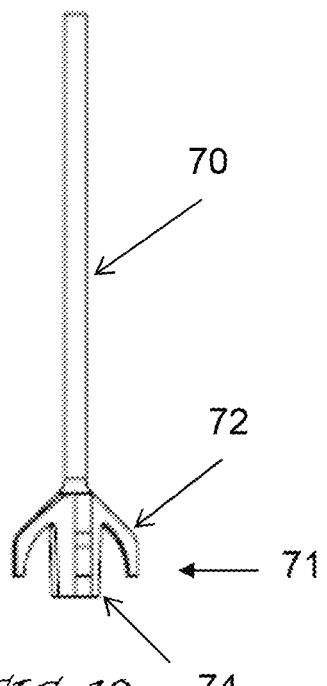
FIG. 18 is a side view of the reamer described in FIG. 17.
Figure 19:
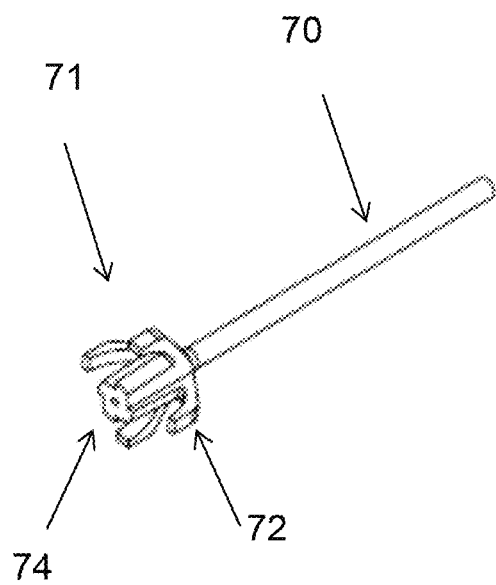
FIG. 19 is a perspective view of the reamer described in FIG. 17.
Figure 17:
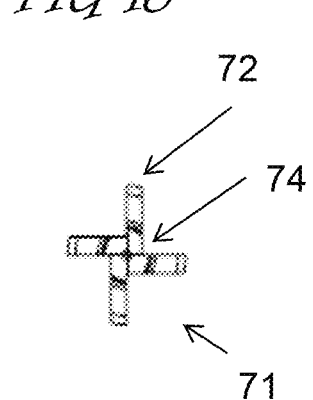
FIG. 17 is a top view of an embodiment of the reamer of the present invention.
Figure 20:
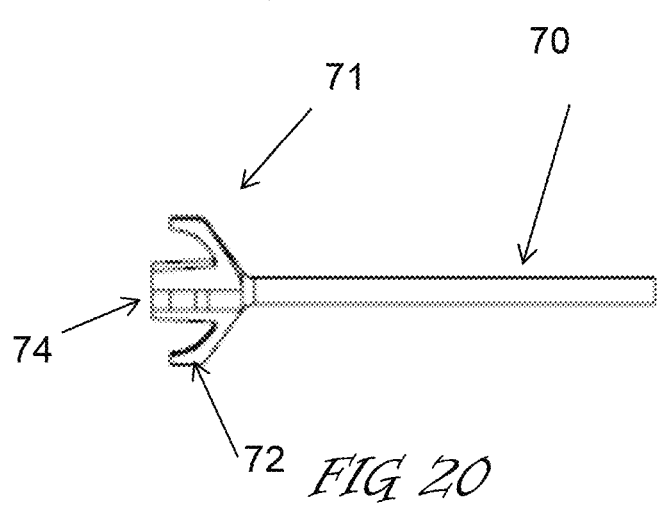
FIG. 20 is another side view of the reamer described in FIG. 17.
Figure 22:
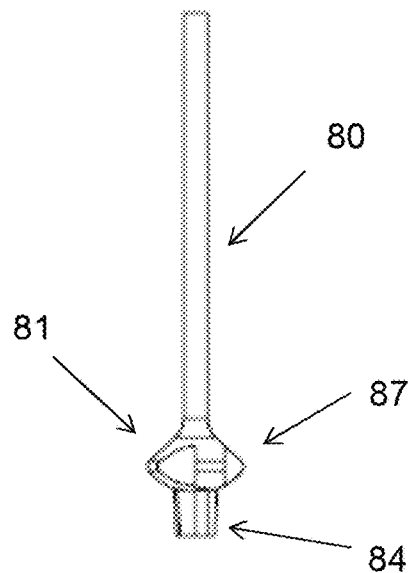
FIG. 22 is a side view of the reamer described in FIG. 21.
Figure 23:
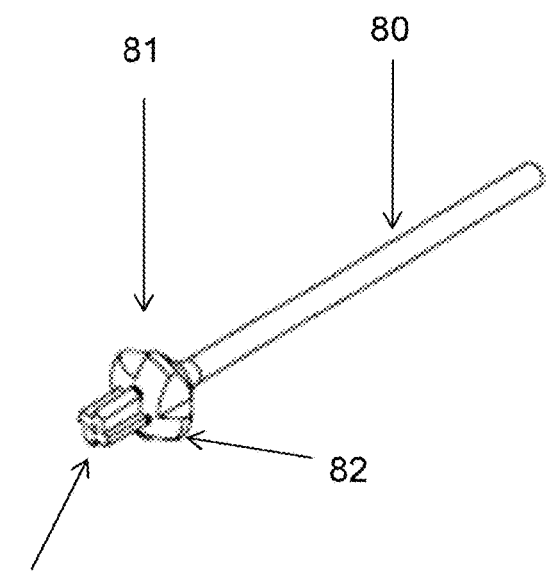
FIG. 23 is a perspective view of the reamer described in FIG. 21.
Figure 21:
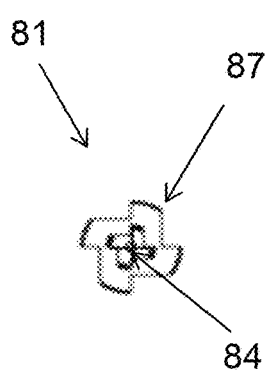
FIG. 21 is a top view of another embodiment of the reamer of the present invention.
Figure 24:
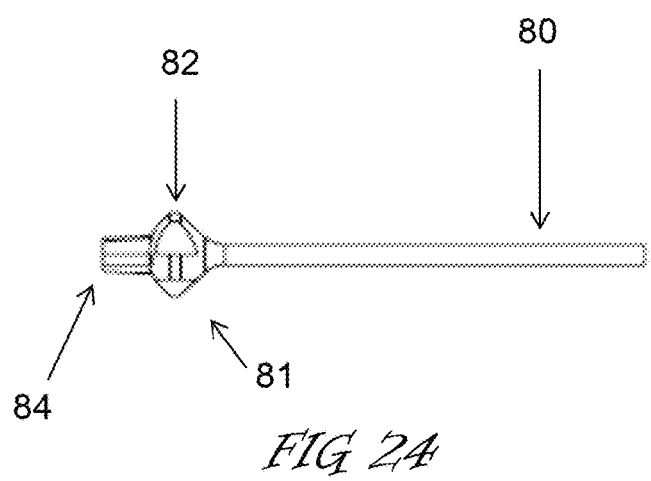
FIG. 24 is another side view of the reamer described in FIG. 21.

FIGS. 14 through 16 disclose another embodiment of the M-Cone. In this embodiment, the distal end 52 of the column 36 is enclosed. The top surface of the dome shape top cover is concave near its center along the diagonal cross-section line AD (FIG. 15) while the top surface is convex along the cross-section line AB (FIG. 16). Similarly, the distal end of the P-Cone's column may also be enclosed.

Figure 25:
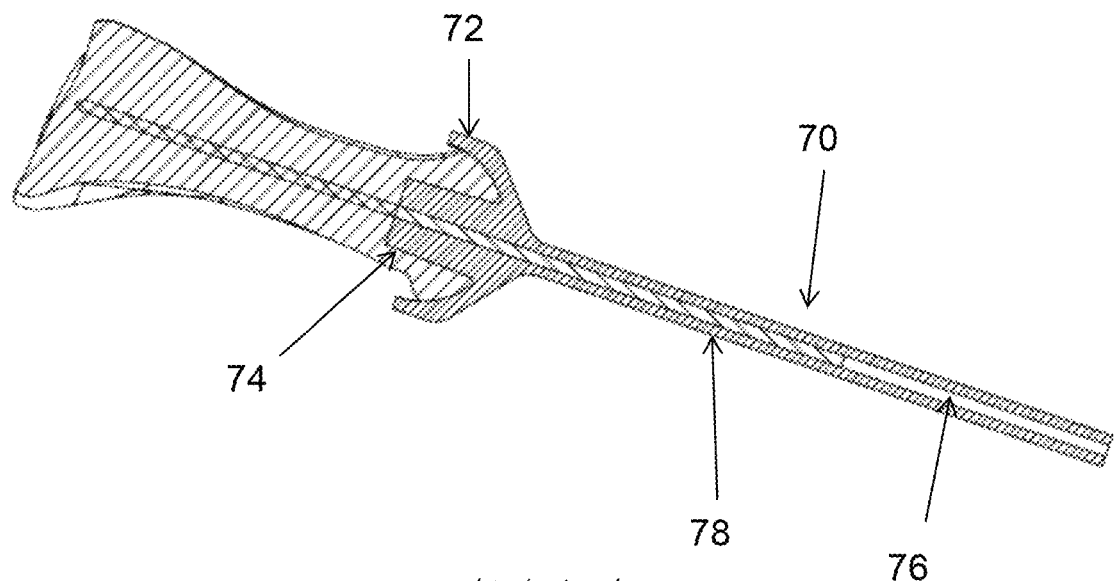
FIG. 25 is a cross-section view showing the reamer described in FIG. 19 on a metatarsal bone.

FIGS. 17 through 20 disclose an embodiment of a reamer for the M-Cone of the present invention. The reamer will ream a metatarsal canal for the insertion of M-Cone. As shown in FIGS. 17 through 20, the reamer includes a cannulated shaft 70, and a head portion 71 arranged in a cross configuration wherein there is one protruding prong 72 at each end of the cross configuration and a flat-top cross protrusion 74 at the center of the cross configuration 71. As illustrated in FIG. 25, the prongs 72 reams the surface of a metatarsal bone, and the flat-top cross protrusion 74 reams a canal for the insertion of M-Cone. The cannulated shaft 70 includes a passage 76 that allows a K Wire 78 to pass through and reach the inner portion of the metatarsal bone.

Figure 26:
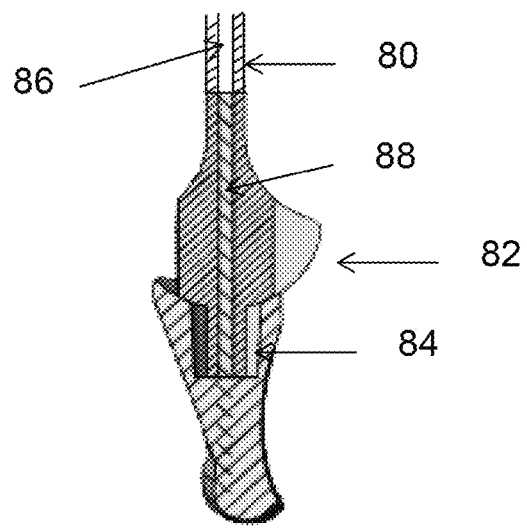
FIG. 26 is a cross-section view showing the reamer described in FIG. 23 on a phalanx bone.

FIGS. 21 through 24 disclose an embodiment of a reamer for the P-Cone of the present invention. The reamer will ream a phalangeal canal for the insertion of P-Cone. As shown in FIGS. 21 through 24, the reamer includes a cannulated shaft 80, and a head portion 81 arranged in a cross configuration wherein each end of the cross configuration 82 bulges outwardly in a semi-elliptical form. A flat-top cross protrusion 84 is located at the center of the cross configuration 81. As illustrated in FIG. 26, the cross end 82 reams the surface of a phalanx bone, and the flat-top cross protrusion 84 reams a canal for the insertion of P-Cone. The cannulated shaft 80 includes a passage 86 that allows a K Wire 88 to pass through and reach the inner portion of the metatarsal bone.

To practice the present invention, a dorsal incision is first made over a MTP joint. Soft tissue dissection down to the joint will be done and the joint will be exposed. The proximal phalanx will be plantarflexed to allow insertion of a K Wire (e.g., 0.062 K Wire) down the first metatarsal shaft. The dual function metatarsal cannulated reamers will be used to drill over the wire, preparing both a dome surface as well as a cone shaped canal in preparation to receive a prosthetic implant. With the proximal phalanx in the same position, a K Wire (e.g., 0.062 K Wire) is then placed down the canal of the phalanx, and dual function reamers are used here as well. A trial prosthesis may be placed into the joint and range of motion and fit are assessed. The surgeon should err on under reaming (taking less bone) and if the fit is too tight, more bone can be taken, usually from the metatarsal side. Once the fit of the trial prosthesis is satisfied, then the cone extensions will be placed in the metatarsal and phalanx. The silastic implant is then introduced. Copious irrigation follows with closure of the wound.

The previous description of the disclosed examples is provided to enable any person of ordinary skill in the art to make or use the disclosed method and apparatus. Various modifications to these examples will be readily apparent to those skilled in the art, and the principles defined herein may be applied to other examples without departing from the spirit or scope of the disclosed apparatus. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope. Skilled artisans may implement the described functionality in varying ways for each particular application, but such implementation decisions should not be interpreted as causing a departure from the scope of the disclosed apparatus.

What is claimed is:

1. A method for practicing a dome toe resurfacing system for metatarsophalangeal joint replacement comprising the steps of:
   (a) performing a dorsal incision over a metatarsophalangeal joint comprising a metatarsal bone and a phalanx bone;
   (b) performing soft tissue dissection and expose the metatarsophalangeal joint;
   (c) using a cannulated reamer to drill down the shaft of the metatarsal bone and insert a K wire down the shaft of the metatarsal bone, and using the cannulated reamer to prepare a dome shape canal in the metatarsal bone for receiving a first cone extension;
   (d) using the cannulated reamer to drill down the shaft of the phalanx bone and insert the K wire down the shaft of the phalanx bone, and using the cannulated reamer to prepare a cone shape canal in the phalanx bone for receiving a second cone extension;
   (e) preparing an elastomeric prosthetic implant comprising a middle element, a first protrusion and a second protrusion, wherein the first protrusion and the second protrusion are located on opposite sides of the middle element;
(f) inserting the first cone extension into the dome shape canal;
(g) inserting the second cone extension into the cone shape canal;
(h) inserting the elastomeric prosthetic implant between the metatarsal bone and the phalanx bone by inserting the first protrusion into the first cone extension and inserting the second protrusion into the second cone extension; and
(i) performing closure of the dorsal incision,
wherein:
the first cone extension comprises a first top cover, a first hollow column of substantially square shape connected to the first top cover having a first canal extending along the centerline of the first hollow column; wherein the first hollow column includes one or more rounded corners and one or more ridges located at the rounded corners transverse to the longitudinal length of the first hollow column; the first top cover comprises a concave undersurface configured to cap an end of a metatarsal bone that joins a phalanx bone, and a dome-shape top surface; wherein the dome-shape top surface includes a concave surface near the center of the first top cover and along a diagonal line of the first hollow column; wherein the contour of the dome-shape top surface mimics the natural anatomy of articular surface of the metatarsal bone;

the second cone extension comprises a second top cover, a second hollow column of substantially square shape connected to the second top cover having a second canal extending along the centerline of the second hollow column; wherein the second hollow column includes one or more rounded corners and one or more ridges located at the rounded corners transverse to the longitudinal length of the second hollow column; the second top cover comprises a convex undersurface configured to cap an end of the phalanx bone that joins the metatarsal bone, and a concave top surface; wherein the contour of the concave top surface mimics the natural anatomy of articular surface of the phalanx bone.

* * * * *